US011857232B2

(12) United States Patent
Weiner et al.

(10) Patent No.: US 11,857,232 B2
(45) Date of Patent: Jan. 2, 2024

(54) FRACTURE FIXATION SYSTEM AND METHOD

(71) Applicant: NEXTREMITY SOLUTIONS, INC., Warsaw, IN (US)

(72) Inventors: Lon S. Weiner, Rumson, NJ (US); John R. Pepper, Warsaw, IN (US); Stuart D. Katchis, Warsaw, IN (US); Ryan Schlotterback, Warsaw, IN (US)

(73) Assignee: MEDARTIS AG, Basel (CH)

( * ) Notice: Subject to any disclaimer, the term of this patent is extended or adjusted under 35 U.S.C. 154(b) by 69 days.

(21) Appl. No.: 17/180,019

(22) Filed: Feb. 19, 2021

(65) Prior Publication Data

US 2021/0315617 A1     Oct. 14, 2021

Related U.S. Application Data

(63) Continuation of application No. 16/910,328, filed on Jun. 24, 2020.

(60) Provisional application No. 62/905,017, filed on Sep. 24, 2019, provisional application No. 62/865,676, filed on Jun. 24, 2019.

(51) Int. Cl.
*A61B 17/82* (2006.01)
*A61B 17/80* (2006.01)

(52) U.S. Cl.
CPC .............. *A61B 17/82* (2013.01); *A61B 17/80* (2013.01)

(58) Field of Classification Search
CPC ...................................................... A61B 17/82
See application file for complete search history.

(56) References Cited

U.S. PATENT DOCUMENTS

| 5,116,340 A | 5/1992 | Songer et al. |
| 5,190,545 A | 3/1993 | Corsi et al. |
| 5,415,658 A * | 5/1995 | Kilpela ................ A61B 17/842 606/300 |
| 5,665,089 A * | 9/1997 | Dall ...................... A61B 17/80 606/908 |
| 5,693,046 A | 12/1997 | Songer et al. |

(Continued)

FOREIGN PATENT DOCUMENTS

| CN | 204484284 U | 7/2015 |
| DE | 20203174 U1 | 7/2002 |

(Continued)

OTHER PUBLICATIONS

"Locking Plate Fixation of Periprosthetic Femur Fractures with and without Cerclage Wires", N.A. Ebraheim, MD, 2013 Chinese Orthopaedic Association and Wiley Publishing Asia Pty Ltd, pp. 183-187.

(Continued)

*Primary Examiner* — Olivia C Chang
(74) *Attorney, Agent, or Firm* — Heslin Rothenberg Farley & Mesiti P.C.; Victor A. Cardona, Esq.

(57) ABSTRACT

A fracture fixation system includes a plate having a laterally extending bore passing therethrough and configured to receive a first wire when the plate is placed in contact with a bone. The plate has a recess for receiving and securing a first end of a first wire, and includes an entry hole and an exit hole to at opposite ends of a first bore to allow the first wire to pass through the plate. A screw is configured to capture said the wire in the first bore to maintain a desired tension on the first wire.

15 Claims, 8 Drawing Sheets

(56) References Cited

U.S. PATENT DOCUMENTS

| | | |
|---|---|---|
| 5,702,399 A | 12/1997 | Kilpela et al. |
| 5,902,305 A | 5/1999 | Beger et al. |
| 5,993,452 A | 11/1999 | Vandewalle |
| 7,229,444 B2 | 6/2007 | Boyd |
| 7,731,718 B2 | 6/2010 | Schwammberger et al. |
| 8,685,025 B2 | 4/2014 | Anapliotis |
| 8,764,809 B2 | 7/2014 | Lorenz et al. |
| 9,138,245 B2 | 9/2015 | Mebarak |
| 9,693,812 B2 | 7/2017 | Zeetser et al. |
| 2008/0234679 A1 | 9/2008 | Sarin et al. |
| 2009/0105717 A1* | 4/2009 | Bluechel ............... A61B 17/82 606/103 |
| 2011/0087225 A1 | 4/2011 | Fritzinger |
| 2014/0243841 A1* | 8/2014 | Cavallazzi ............. A61B 17/74 606/103 |
| 2016/0038199 A1 | 2/2016 | Wiederkehr et al. |
| 2017/0181780 A1 | 6/2017 | Cremer et al. |
| 2018/0161083 A1 | 6/2018 | Kobayashi |
| 2019/0133653 A1 | 5/2019 | Swarts |

FOREIGN PATENT DOCUMENTS

| | | |
|---|---|---|
| GB | 2257913 A | 1/1993 |
| JP | H07506988 A | 8/1995 |
| KR | 20160058515 A | 5/2016 |
| WO | 9318716 A1 | 9/1993 |
| WO | 2006135935 A1 | 12/2006 |

OTHER PUBLICATIONS

"Vascular complication after percutaneous femoral cerclage wire" M. Ehlinger, Orthopaedics & Traumatology: Surgery & Research 104 (2018), pp. 377-381.

UK Search Report dated Dec. 8, 2020.

First Office Action dated Sep. 14, 2023, Japanese Patent Application No. 2020-213120, 4 pp.

* cited by examiner

FRACTURE FIXATION SYSTEM AND METHOD

CROSS-REFERENCE TO RELATED APPLICATIONS

This application is a continuation of U.S. patent application Ser. No. 16/910,328 filed Jun. 24, 2020, which claims priority to U.S. provisional application No. 62/865,676 filed Jun. 24, 2019, entitled CERCLAGE SYSTEM AND METHOD, and U.S. provisional application No. 62/905,017 filed Sep. 24, 2019, entitled FRACTURE FIXATION SYSTEM AND METHOD, which are incorporated herein by reference in their entirety.

BACKGROUND OF THE INVENTION

Background Information

Femoral fractures may occur naturally or iatrogenically during total hip arthroplasty. Depending on the fracture pattern, cerclage alone, cerclage with a plate or plates, cerclage with a strut, cerclage with an extended hip stem, or cerclage with a combination of plates, struts, and/or extended hip stems may be used for bone fixation. However, a problem with cerclage is that it may create poor bone unions without using additional support devices. In particular with total hip arthroplasty using additional support may not be desirable or possible. With femoral fractures, there may be a high load on the cerclage wires resulting in adjacent boney erosion and loss of fixation due to wire migration.

There is a need for a cerclage device that provides improved bone unions while providing for cerclage wire tensioning.

SUMMARY OF THE INVENTION

These, and other objects, features and advantages of this invention will become apparent from the following detailed description of the various aspects of the invention taken in conjunction with the accompanying drawings.

DETAILED DESCRIPTION OF THE INVENTION

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Figure 1:
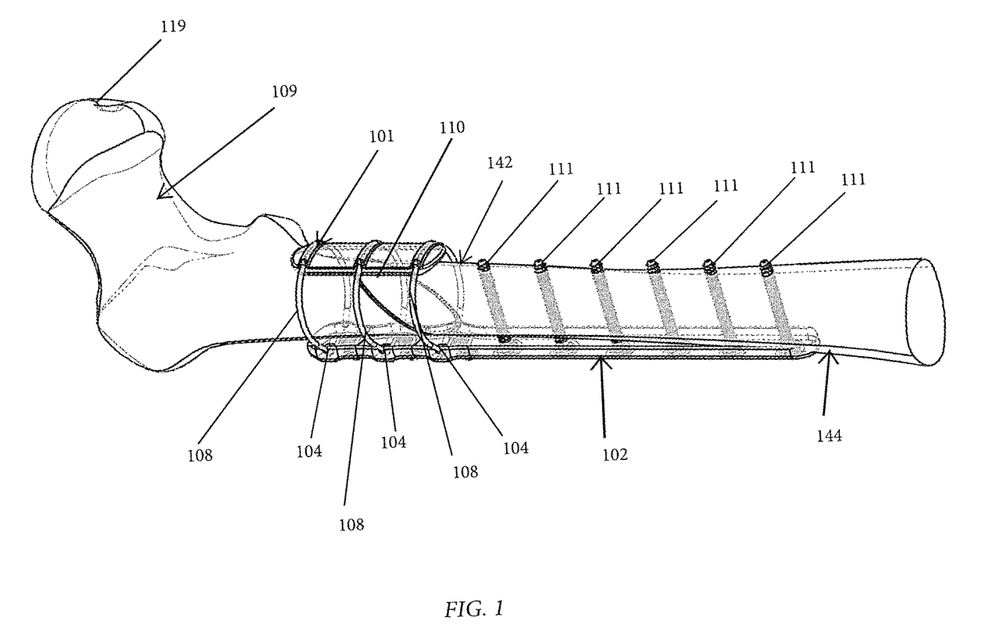
FIG. 1 is a posterior perspective view of a fracture fixation system connected to a femur, in accordance with an aspect of the present invention.
Figure 2:
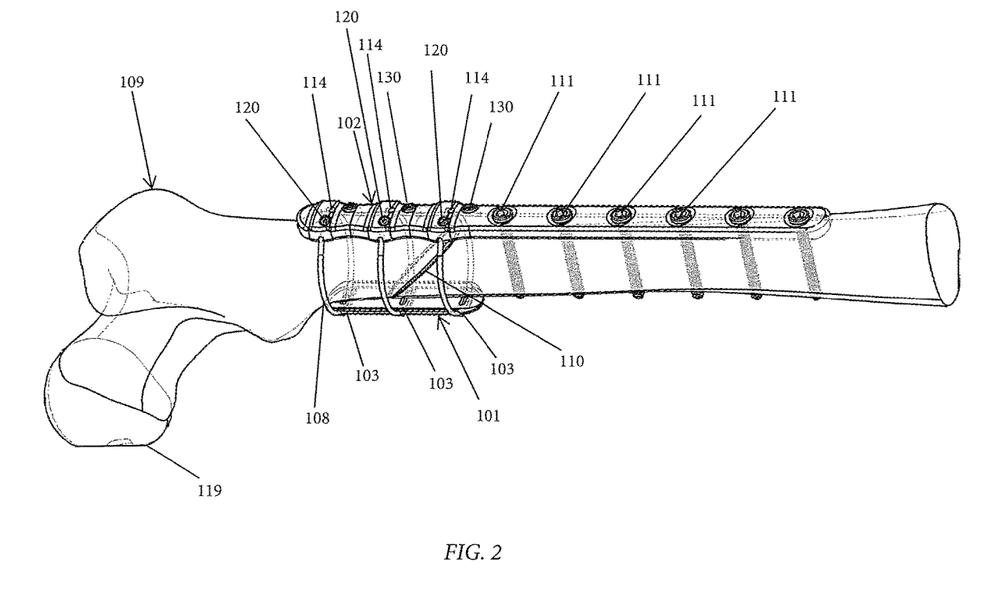
FIG. 2 is an anterior perspective view of the fracture fixation system of FIG. 1 connected to the femur, in accordance with an aspect of the present invention.
Figure 3:
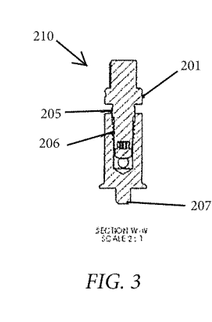
FIGS. 3-6 are various views of a tensioning drum, in accordance with an aspect of the present invention.
Figure 4:
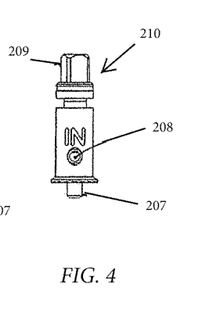
Figure 5A:
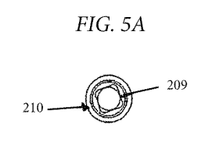
Figure 5B:
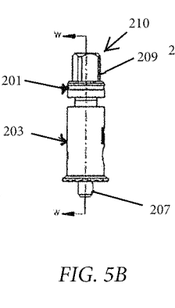
Figure 6:
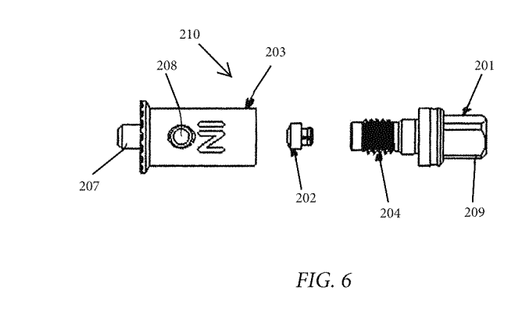
Figure 7:
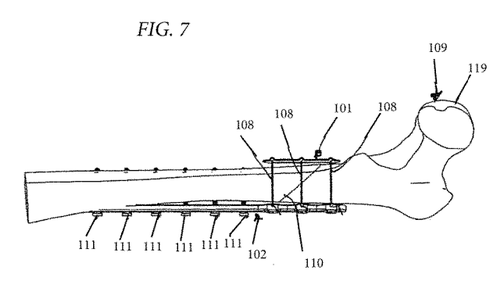
FIGS. 7-10 are various views of the fracture fixation system of FIG. 1 connected to the femur, in accordance with an aspect of the present invention.
Figure 8:
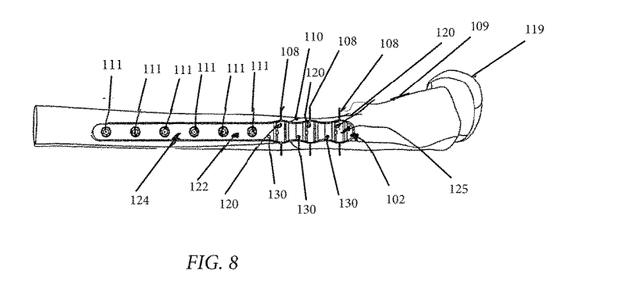
Figure 9:
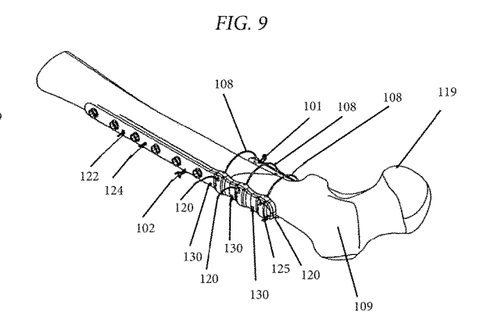
Figure 10:
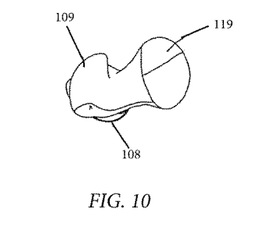
Figure 11:
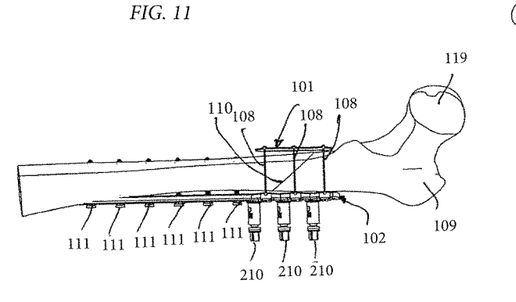
FIGS. 11-14 are various views of the fracture fixation system of FIG. 1 connected to the femur and with tensioning drums affixed to a lateral plate thereof, in accordance with an aspect of the present invention.
Figure 12:
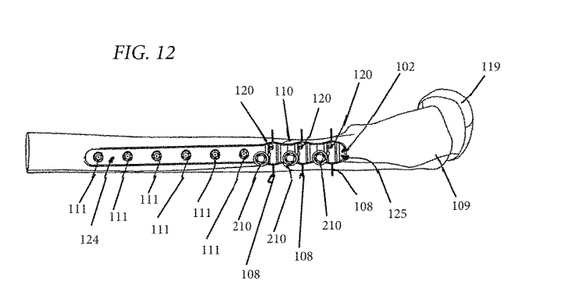
Figure 13:
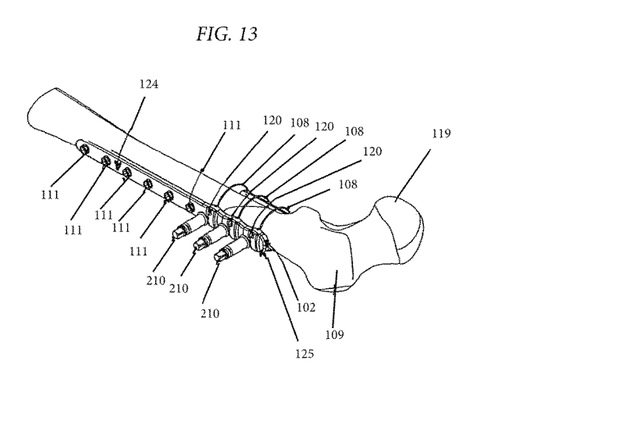
Figure 14:
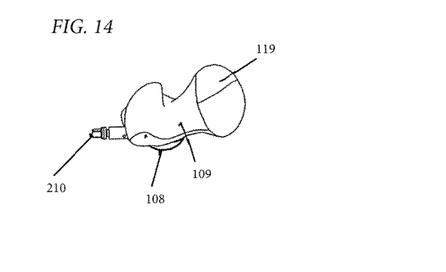
Figure 15:
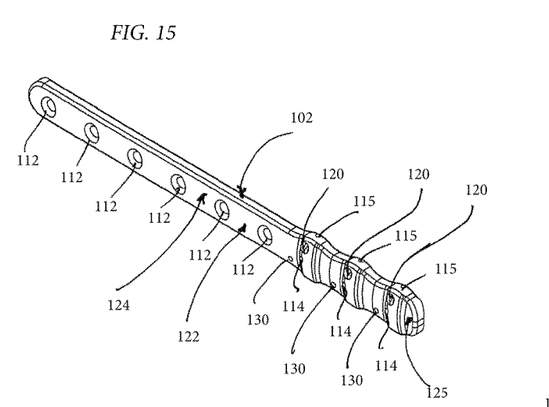
FIGS. 15-19 are various views of the lateral plate of the fracture fixation system of FIG. 1, in accordance with an aspect of the present invention.
Figure 16:
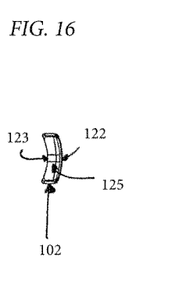
Figure 17:
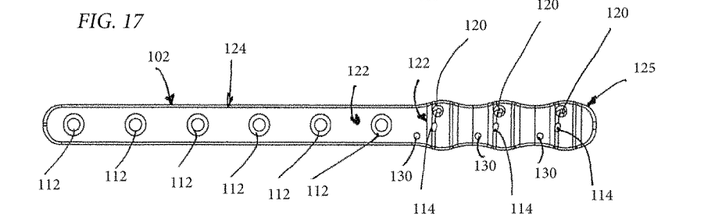
Figure 18:
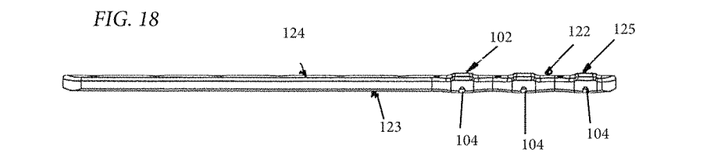
Figure 19:
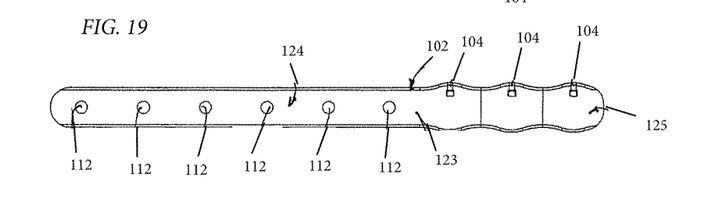
Figure 20:
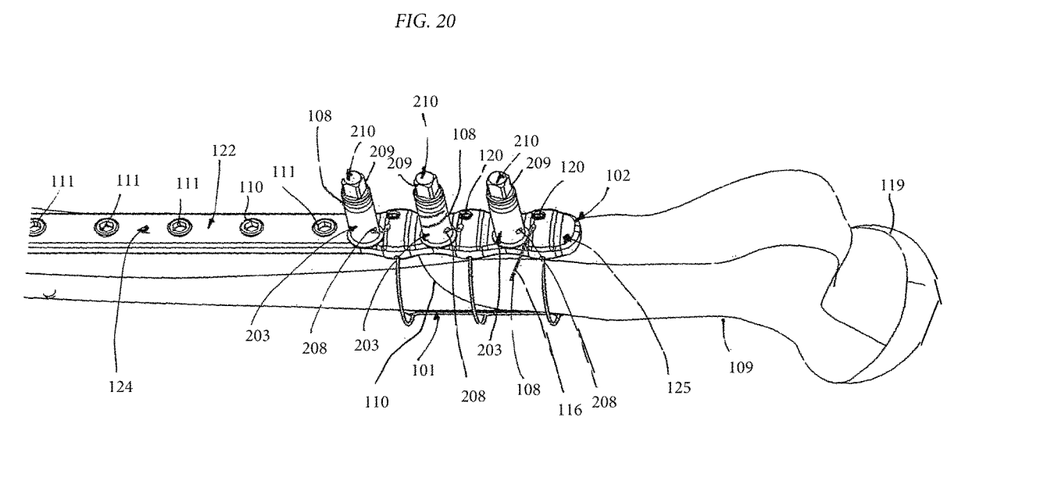
FIG. 20 is a perspective view of the lateral plate with tensioning drums affixed to the fracture fixation system of FIG. 1, in accordance with an aspect of the present invention.
Figure 21:
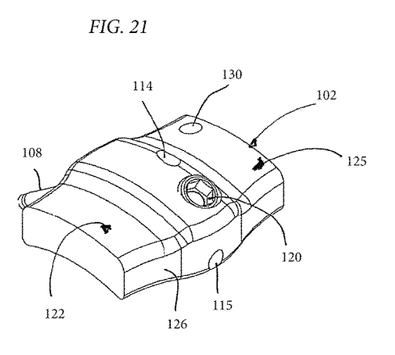
FIGS. 21-25 are various perspective view of a section of the lateral plate of the fracture fixation system of FIG. 1, in accordance with an aspect of the present invention.
Figure 22:
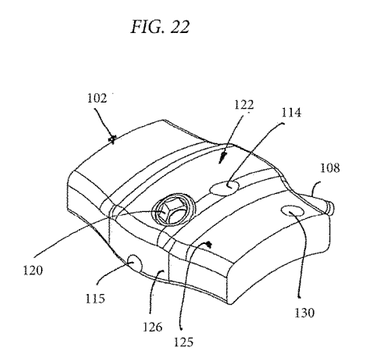
Figure 23:
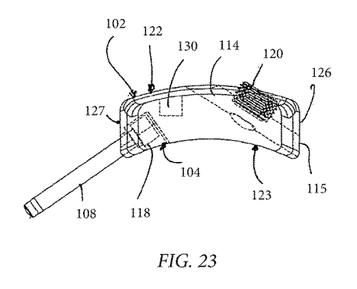
Figure 24:
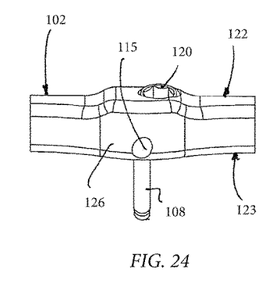
Figure 25:
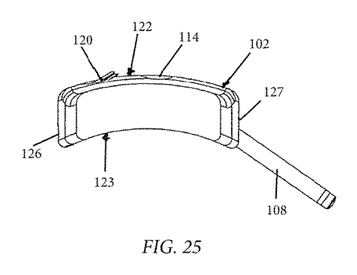

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for use in femoral cerclage fixation. However, those possessing an ordinary level of skill in the relevant art will appreciate that fixation of other bones are suitable for use with the foregoing systems, methods, and apparatuses. Likewise, the various figures, steps, procedures, and work-flows are presented only as an example and in no way limit the systems, methods or apparatuses described to performing their respective tasks or outcomes in different time-frames or orders. The teachings of the present invention may be applied to cerclage related to any bone.

Furthermore, there is no intention to be bound by any expressed or implied theory presented in the preceding technical field, background, brief summary, or the following detailed description. It is also to be understood that the specific devices and processes illustrated in the attached drawings, and described in the following specification, are simply exemplary embodiments of the inventive concepts. Hence, specific dimensions and other physical characteristics relating to the embodiments disclosed herein are not to be considered as limiting, unless expressly stated otherwise.

The various embodiments described herein provide for systems, apparatuses, devices, and methods for fracture fixation. The various figures and description may refer to femoral fracture fixation. However one having ordinary skill in the art will understand that that the following systems, apparatuses, devices, and methods for fracture fixation may be used with specific femoral fractures, such as periprosthetic Vancouver Grade B and distal femoral fractures, or fractures to other bones such as greater trochanter fractures; tibial distal, proximal, and mid shaft fractures; humeral head fractures; fibula fractures; olecranon fractures; and other bones with fractures, osteotomies, or deformities needing compressive and/or corrective forces.

Referring to the drawings, wherein like reference numerals are used to indicate like or analogous components throughout the several views, and with particular reference to FIGS. 1-2, 7-10, and 15-19, a fracture fixation system 100 is affixed to a bone or femur 109, with the parts of femur 109 on opposite sides of a fracture 110 having been aligned. Fracture fixation system 100 has a medial plate 101, longitudinally aligned on a medial surface 142 of femur 109 and a lateral plate 102, longitudinally aligned on the lateral surface 144 of femur 109. Medial plate 101 and lateral plate 102 are depicted on opposite sides of femur 109 and connected with a binding or a cerclage wire 108, with fracture 110 being intermediate to medial plate 101 and lateral plate 102. Medial plate 101 may be, for example, a cerclage adjunct device having an elongated plate, with a lateral wire slot or bore 103, and having a lateral curvature approximating a circumferential curvature of medial surface 142 of femur 109. Lateral plate 102 may also have a curvature, for example, approximating a circumferential curvature of a lateral surface of femur 109. Lateral plate 102 may be, for example, further connect to femur 109 with a bone screw 111 inserted through lateral plate 102 and into femur 109, with bone screw 111 positioned inferior to fracture 110. Bone screw 111 may for example, extend through lateral plate 102 and through medial surface 142 of femur 109.

With continued reference to FIGS. 1-2, 7-10, and 15-19, lateral plate 102 further has a first section 125, a second section 124, a top side 122, a bottom side 123, a first side 126, and a second side 127. First section 125 may be, for example, connected to medial plate 101 and around fracture 110 with cerclage wire 108. First section 125 has a set screw 120 received in threaded opening, cerclage wire bore or cerclage wire entry hole 115, a wire exit hole 114, a post hole 130, and a wire attachment undercut or a tethering recess 104. Second section 124 extends longitudinally away from first section 125 distal to a femur head 119. Second section 124 may have, for example, a plurality of holes 112 through which a plurality of bone screws (e.g., multiple instances of bone screw 111) may be inserted into femur 109.

With reference to FIGS. 3-6 and 20, a drum 210 has a threaded connection 206 between a lower end 203 with a threaded opening 205, engaged with an upper end or driving end 201 with threading 204. Driving end 201 is depicted as having a screw head 209, which may, for example, be square shaped and engageable with a nut driver or other tool for driving drum 210. Driving end 201 may be rotated, for example, in a clockwise direction by hand or such a nut driver. Rotation of driving end 201, may, for example, close driving end 201 and lower end 203 together. Cerclage wire 108 may be threaded through a cross hole 208 such that rotating driving end 201 may, for example, clamp cerclage wire 108 between lower end 203 and driving end 201, keeping cerclage wire 108 stationary. Drum 210 may further have, for example, a bushing 202, positioned between lower end 203 and driving end 201 such that rotating driving end 201 exerts linear pressure onto cerclage wire 108 without translating rotational motion. Such linear pressure may be, for example, used to maintain cerclage wire 108 position in cross hole 208 due to friction where cerclage wire 108 contacts and is located between bushing 202 and lower end 203. Continued rotation of driving end may, for example, rotate drum 210 with cerclage wire 108 extended through hole 208 thereby causing cerclage wire 108 to be wound around drum 210, thereby causing tension in cerclage wire 108 to be increased. During rotation of drum 210, linear pressure is maintained by bushing 202 on cerclage wire 108, without adding rotation pressure to cerclage wire 108 within drum 210. Adjusting and maintaining tension may aid in holding bone fragments in place during a surgical procedure and after when subjected to anatomic loading.

As depicted in FIGS. 21-25, with reference to first section 125 of lateral plate 102, cerclage wire entry hole 115 is depicted positioned on a first side 126 and wire exit hole 114 is positioned on top side 122. Wire entry hole 115 and wire exit hole 114 extend to meet through lateral plate first section 125, creating an oblique hole or tunnel therebetween. Set screw 120 is depicted inset into top side 122, intersecting with the bore between wire entry hole 115 and wire exit hole 114. Cerclage wire 108 is depicted with a cerclage wire head or a cerclage wire first end 118 and a free end 116. Tethering recess 104 may be, for example, a slot or opening extending from bottom side 123 to second side 127, configured (e.g., shaped and dimensioned) to capture cerclage wire head 118, when cerclage wire 108 is under tension. Post hole 130 extends from top side 125 towards bottom side 124 and is configured (e.g., shaped and dimensioned) to accept insertion of post 207 of drum 210.

With reference to FIGS. 1-25, a method of fracture fixation includes aligning opposing sides of fracture 110 and affixing lateral plate 102 to lateral surface 144. Cerclage wire first end 118 may be inserted into tethering recess 104. Free end 116 may be, for example, inserted through lateral wire slot 103 of medial plate 101, with medial plate 101 placed onto medial surface 142. Free end 116 may, for example, continue around femur 109 and be inserted into entry hole 115, exiting through exit hole 114. Drum 210, may, for example, be engaged with lateral plate 102, with post 207 inserted into post hole 130. Free end 116 may be inserted through cross hole 208 and rotating upper drive end 201 imparts a clamping, linear force onto cerclage wire 108, without rotational motion. Cerclage wire 108 may then be tensioned by winding free end 116 of cerclage wire 108 around drum 210 and turning upper drive 201 and rotating drum 210 to further wind cerclage wire 108. Such rotation may impart tension to cerclage wire 108 and set cerclage wire 118 into tethering recess 104. Once the desired tension is reached, set screw 120 may be tightened (e.g., into a threaded hole in lateral plate 102) to capture or clamp cerclage wire 108 within the hole extending from entry hole 115 to exit hole 114. To maintain tension on cerclage wire 108, free end 116 thereof may be, for example, placed in a crimp (not shown) or holder on or adjacent to lateral plate 102.

With reference to FIGS. 1-25, a plurality of cerclage wires (e.g., multiple instances of cerclage wire 108) may, for example, be used to engage medial plate 101 and lateral plate 102. A plurality of bone screws (e.g., multiple instances of bone screw 111) may, for example, be inserted into plurality of bone screw holes 112 to affix lateral plate 102 to femur 109. As depicted, medial plate 101 may have, for example, a plurality of lateral wire slots (e.g., multiple instances of wire slot 103). Medial plate 101, may be, for example, a two wire cerclage adjunct device or a three wire cerclage adjunct device. As further depicted, lateral plate 102 may have, for example, a plurality of set screws (e.g., multiple instances of set screw 120), a plurality of cerclage entry holes (e.g., multiple instances of cerclage wire entry hole 115), a plurality of wire exit holes (e.g., multiple instances of wire exit hole 114), a plurality of post holes (e.g., multiple instances of post hole 130), and a plurality of tethering recesses (e.g., multiple instances of tethering recess 104).

In other embodiments of fracture fixation system 100, may have, for example, at least two plates of the kind described by medial plate 101 and/or lateral plate 102.

Aspects of the invention described herein include bone fixation of fractures to promote bone fusion in femur 109. Those same aspects also include bone fixation of fracture to promote bone fusion in a femur having a hip replacements stem (not shown) inserted into femur 109.

While several aspects of the present invention have been described and depicted herein, alternative aspects may be effected by those skilled in the art to accomplish the same objectives. Accordingly, it is intended to cover all such alternative aspects as fall within the true spirit and scope of the invention.

What is claimed is:

1. A fracture fixation system comprising:
   a plate having a laterally extending bore passing therethrough, the laterally extending bore configured to receive a first wire when the plate is placed in contact with a bone;
   said plate having a recess for receiving and securing a first end of said first wire;
   said plate comprising an entry hole and an exit hole to at opposite ends of a first bore to allow said first wire to pass through said plate; and
   a screw to capture said first wire in said first bore to maintain a desired tension on said first wire,
   a tightener configured to provide tension to the first wire, said tightener comprising a post configured to be received in a post hole of said plate and a cross bore configured to allow the first wire to pass therethrough such that the tightener may be rotated in the post hole to tighten the first wire around the tightener.

2. The system of claim 1 wherein said first bore is a first bore of a plurality of laterally extending bores passing through said plate and said first wire is a first wire of plurality of a wires passing through said plurality of bores to connect said plate to the bone to hold the bone.

3. The system of claim 1 further comprising a second plate located on an opposite side of the bone and having a second bore configured to allow the first wire to pass therethrough to secure the first plate and the second plate to the bone when the wire is tightened.

4. The system of claim 1 wherein said tightener comprises a lower end and a driving end threadingly engageable with each other such that said driving end is threaded into a cavity of said lower end.

5. The system of claim 4 wherein said lower end comprises a bore entry and a bore exit bounding said cross bore.

6. The system of claim 5 further comprising a bushing between said lower end and said driving end to hold said first wire in said cross bore and to inhibit movement of said first wire in said cross bore.

7. The system of claim 6 wherein said bushing imparts a clamping linear force on said first wire when said lower end threadingly engages said driving end.

8. The system of claim 1 wherein said plate comprises a first portion comprising said plurality of laterally extending bores and a second portion comprising a plurality of openings receiving a plurality of screws to connect said plate to the bone.

9. A method of cerclage fixation comprising:
   aligning opposing portions of a fractured bone to set the bone;
   placing a plate on the fractured bone;
   attaching a first end of a wire to the plate and passing the wire around the bone;
   passing the wire through a bore of the plate from an entry hole to an exit hole;
   tightening the wire to apply tension to the bone; and
   securing a second end of the wire to the plate;
   wherein the tightening comprises passing said wire through a cross bore of a tightener having an end received in a post hole of said plate and rotating said tightener to provide a tension to said wire.

10. The method of claim 9 wherein said bore is a first bore of a plurality of laterally extending bores passing through said plate and further comprising connecting ends of a plurality of other wires to said plate, passing said other wires through said plurality of laterally extending bores and connecting opposite ends of said plurality of other wires to said plate to secure the bone.

11. The method of claim 9 wherein attaching said first ends of said wire comprises inserting said first wire in a recess of said plate and connecting said second end comprises connecting said second end to said plate using a screw.

12. The method of claim 9 wherein said tightener comprises comprises a lower end and a driving end threadingly engageable with each other such that said driving end is threaded into a cavity of said lower end.

13. The method of claim 12 wherein said tightener comprise a a bushing between said lower end and said driving end, and further comprising engaging said driving end to said lower end to hold said wire in a bushing between said lower end and said driving end to movement of said first wire in said cross bore.

14. The method of claim 1 wherein the passing the wire around the bone comprises passing the wire through a second bore of a second plate on an opposite side of the bone relative to the plate.

15. The method of claim 1 further comprising securing the plate to the bone by a screw through an opening in said plate.

* * * * *